United States Patent
Walele et al.

(10) Patent No.: US 6,464,991 B1
(45) Date of Patent: Oct. 15, 2002

(54) OAT LIPID BASED SURFACTANTS AND DERIVATIVES AND PROCESS FOR PREPARING SAME

(75) Inventors: Ismail I. Walele, Saddle Brook, NJ (US); Samad A. Syed, Paramus, NJ (US)

(73) Assignee: Finetex, Inc., Elmwood Park, NJ (US)

( * ) Notice: Subject to any disclaimer, the term of this patent is extended or adjusted under 35 U.S.C. 154(b) by 0 days.

(21) Appl. No.: 09/556,741

(22) Filed: Apr. 21, 2000

Related U.S. Application Data

(60) Provisional application No. 60/132,474, filed on May 4, 1999.

(51) Int. Cl.$^7$ ............................. A61K 7/00; A61K 7/06
(52) U.S. Cl. ..................... 424/401; 424/70.1; 424/750; 514/844; 514/880
(58) Field of Search .......................... 424/59, 70.1, 750, 424/401, 725; 514/553, 554, 557, 558, 561, 844, 880

(56) References Cited

U.S. PATENT DOCUMENTS

| | | | |
|---|---|---|---|
| 4,014,995 A | | 3/1977 | Juliano et al. |
| 4,089,848 A | | 5/1978 | Bell et al. |
| 4,211,695 A | | 7/1980 | Oughton |
| 4,211,801 A | | 7/1980 | Oughton |
| 4,430,245 A | * | 2/1984 | Beattie |
| 4,834,768 A | * | 5/1989 | Grollier |
| 5,026,548 A | | 6/1991 | Evans et al. |
| 5,545,398 A | | 8/1996 | Perricone |
| 5,552,135 A | | 9/1996 | Cioca et al. |
| 5,589,195 A | | 12/1996 | Potter |
| 5,616,332 A | | 4/1997 | Herstein |
| 5,620,692 A | * | 4/1997 | Potter |
| 5,622,690 A | | 4/1997 | Potter et al. |
| 5,750,748 A | * | 5/1998 | Boutique |
| 5,773,397 A | | 6/1998 | Tuanara |
| 5,817,608 A | | 10/1998 | Bell |
| 5,863,945 A | | 1/1999 | Murayama et al. |
| 5,888,515 A | | 3/1999 | Albert et al. |
| 5,888,521 A | | 3/1999 | Zimmerman |

OTHER PUBLICATIONS

Nurture, Inc. "Compositional Profiles":Typical Microat® AFA Complex Fatty Acid Composition, 10/94 (2 pgs); Microat® AFA Complex, INCI Name, Oat Extract, 01/95 (1 pg.); Typical Microat® AFA Complex Antioxidants Composition, 05/95 (1pg.).

* cited by examiner

Primary Examiner—Gollamudi S. Kishore
(74) Attorney, Agent, or Firm—Weingram & Associates, P.C.

(57) ABSTRACT

Novel oat-lipid based derivatives, surfactants and emollients are disclosed, as well as their use in the production of surface active derivatives or non-surface active esters, and ester emollients. The surfactants and fatty derivatives are useful as emollients, dispersants, emulsifiers, and conditioners for hair care and skin care products. For example, derivatives such as amides of oat fatty triglycerides ("OFTG")/Monoethanolamine; Acyl Amidopropyl Dimethyl Amines of OFTG as Cationic Surfactants; Betaines based on OFTG; Esters of OFTG based Fatty Acids and Isostearyl Alcohol; Quaternaries based on OFTG based Amido-propyl Dimethyl Amine; Sulfosuccinamates based on OFTG—MEA Amides; and Sulfosuccinamates based on OFTG—Iso Propanolamines have been prepared. Derivatives may also include those involving other reactive groups known to those skilled in the art.

8 Claims, No Drawings

OAT LIPID BASED SURFACTANTS AND DERIVATIVES AND PROCESS FOR PREPARING SAME

This application claims benefit of No. 60/132,474 filed May 4, 1999.

BACKGROUND OF THE INVENTION

1. Field of the Invention

The present invention relates to novel oat-lipid based surfactants and derivatives, and emollients, their process of manufacture, their use in the production of surface active derivatives, non-surface active esters, and ester emollients, and skin and hair care preparations containing the surfactants, derivatives, and emollients. The surfactants and fatty ester derivatives are useful as emollients, dispersants, emulsifiers, and conditioners for hair care and skin care products.

2. Description of the Related Art

Surfactants and derivatives are known for a variety of different applications for cosmetic, pharmaceutical, and medicinal purposes.

Numerous references describe the production and use of surface active derivatives or non-surface active esters, and ester emollients. For example, it is known to use oats and oat extract in cosmetic preparations to obtain the benefits of mildness, antioxidant properties, etc. Surfactants and fatty derivatives useful as emollients, dispersants, emulsifiers and conditioners for hair and skin care products are commonly produced from a wide variety of fatty acids, fatty alcohols and amines, polyamines, dialkyl propylamines, alkanolamines, etc. However, none of these references teach or suggest the specific novel oat-based surfactants made from the fatty oil triglyceride obtained from oats, or OFTG, of this invention or the use of OFTG to produce surface active derivatives or non-surface active esters, and ester emollients for cosmetics and personal care products.

More specifically, oat-based compositions are disclosed in U.S. Pat. Nos. 5,620,692 and 5,622,690 to Potter et al. assigned to Nurture, Inc. of Missoula, Mont. The disclosures of these patents are incorporated herein by reference.

U.S. Pat. No. 5,620,692 to Potter et al. discloses a process for preparing oat oil compositions having antioxidant and dermatological properties.

U.S. Pat. No. 5,622,690 to Potter et al. discloses a method for reducing sunburn by applying a topical formulation comprising an amount of a free flowing seed derived material, preferably oats, having a protein content of between about 1% to 50%, and a average particle size from 1.0 um to 600 um, to skin prior to exposure to ultraviolet radiation.

U.S. Pat. No. 4,014,995 to Juliano et al. discloses a liquid cosmetic preparation comprising a colloidally stable dispersion of 1 to 10% by weight of oat flour in a liquid vehicle. The oat flour is obtained by grinding oat flakes and screening for the preferred particulate size. The oat flour functions to moisturize the skin.

U.S. Pat. No. 4,211,695 to Oughton discloses a process for separating comminuted oats into fractions such as bran, oat oil, flour and protein-enriched or protein deficient flours, for use in the food industry. The process comprises admixing comminuted dehulled oats with an organic solvent for oat oil, and subjecting the admixture, in the form of a slurry, to centrifugal force.

U.S. Pat. No. 4,211,801 to oughton discloses a process for separating substantially gum-free flour from oats, comprising admixing comminuted oats with a solvent for oil in the oats and separating substantially gum-free flour from the admixture, and recovering oat oil from the solvent. The products are used in the food industry.

U.S. Pat. No. 5,026,548 to Evans discloses a surfactant for use as a viscosity reducing agent in chocolate, produced by extracting oats with an aliphatic alcohol, extracting the alcohol extract with methanol, and evaporating the methanol.

U.S. Pat. No. 5,552,135 to Cioca et al. discloses a sunscreen composition comprising an oat extract, a sunscreening agent, and a vehicle for enabling said composition to be applied to the skin.

U.S. Pat. No. 5,888,515 to Albert et al. discloses a topical composition for treating poison ivy comprising jewelweed extract, plantain leaf extract and a quantity of an aqueous colloidal dispersion of oat grains, in admixture. The colloidal oat dispersion acts as an excipient and delivery agent for the jewelweed and plantain enzymes and provides anti-inflammatory and anti-itch effect.

U.S. Pat. No. 5,589,195 to Potter discloses a method of forming a film on a surface comprising providing a film-forming emulsion comprising an emulsifier consisting essentially of a proteinaceous particulate matter derived from oat seed.

U.S. Pat. No. 5,817,608 to Bell discloses a cleansing composition having a silicone conditioning agent, and refined oats that have been at least partially defatted and from which at least some of the bran has been removed, so that the conditioning agent is carried by the refined oats.

U.S. Pat. No. 5,863,945 to Murayama et al. discloses amide derivatives and skin and hair preparations containing the amide derivatives.

U.S. Pat. No. 5,888,521 to Zimmerman discloses a composition comprising a hydroxycarboxylic acid (such as glycolic, lactic, citric or malic acids) and oat extract, where the oat extract contains less than about 1% beta-glucan. The composition is applied to the skin to increase the rate of skin exfoliation.

However, among the foregoing patents, none disclose or suggest the specific novel oat lipid based surfactants and derivatives of the invention, a process of preparing same, or the use of such derivatives and surfactants having mildness and emolliency for cosmetics and personal care products.

OBJECTS AND SUMMARY OF THE INVENTION

It is an object of the invention is to provide novel oat-based surfactants and derivatives which are made from a naturally renewable source.

It is another object of the present invention to provide surfactants and derivatives which are made from oat fatty triglyceride.

It is another object of the invention to provide novel oat-based surfactants and derivatives for use in hair care, skin care and other personal care products.

It is yet another object of the invention to provide novel oat-based surfactants and derivatives which have a usefulness similar to conventional amides and betaines.

A further object of the invention is to provide novel oat-based surfactants and derivatives for use in skin care products where the skin feel is even better than conventional derivatives.

It is a further object of the invention to provide novel oat-based surfactants and derivatives having mildness and emolliency for use in skin care and hair care products.

Yet a further object of the invention is to provide novel oat-based surfactants and derivatives which inherently possess natural antioxidants and vitamin factors for use in skin care and hair care products.

Yet another object of the invention is to provide novel oat-based surfactants and derivatives having very low to negligible toxicological effects.

Another object of the invention is to provide formulations containing novel oat-based surfactants and derivatives which are very mild and have a very low toxicological profile.

Another object of the invention is to provide low-irritation oat-based surfactants and derivatives for skin care and hair care products.

A still further object of the invention is to provide novel oat-based surfactants and derivatives having a fatty acid composition profile close to that of the principal constituents of human skin surface lipids that play a key role in maintaining the normal barrier function of healthy skin.

Another object of the invention is to provide a method of producing mild, emollient hair care or skin care products using oat-based surfactants and derivatives.

These and other objects are accomplished by providing oat-based surfactants and derivatives which are improved as compared to commercially available surfactants and derivatives, as they are made from a naturally renewable source, namely, oats. The surfactants and derivatives are mild and have antioxidancy activity. Skin and hair care formulations containing the surfactants and derivatives of the invention are mild and emollient, have very low toxicological profiles, and are not irritating to the skin.

DETAILED DESCRIPTION OF THE INVENTION

Major fatty raw materials are fatty triglycerides from sources which are naturally renewable such as coconut oil, soybean oil, castor oil, sunflower oil, corn oil, canola oil, etc. A preferred source is oat seeds.

The surfactants and derivatives and emollients of the invention are made from the fatty oil triglyceride obtained from oats. Such fatty oil triglyceride is called "oat extract" because it is the raw material obtained by extraction of oat seeds of Avena Sativa with organic solvents.

Oat seeds may be refined, unrefined, or minimally refined, as disclosed in U.S. Pat. Nos. 5,622,690 and 5,620,692 to Potter et al., incorporated herein by reference, to free the proteinaceous matter from the lipids. The lipid portion is called "oat extract", "oat fatty oil" or "oat fatty triglyceride", abbreviated herein as "OFTG", commercially available from Nurture, Inc., of Missoula, Mont. as Microat® afa Complex.

Oat Fatty Triglyceride (OFTG) is essentially made up of saturated and unsaturated fatty acids along with some free fatty acids. It is well known that OFTG contains a high level of natural potent antioxidants, such as an ester of ferulic acid. This compound is structurally similar to the synthetic antioxidants butylated hydroxyanisole (BHA) and butylated hydroxytoluene (BHT). Additionally, OFTG from oat extract contains tocols including tocopherols and tocotrienols. Furthermore, OFTG contains the three forms of Vitamin E (alpha-, gamma- & delta-tocopherols). It is also known that OFTG contains phenols and phospholipids which behave as antioxidants. Antioxidants scavenge and neutralize free radicals created by normal metabolism or damage to skin cells which may result from exposure to ultraviolet radiation, inflammation, dry skin, psoriasis, dermatitis, burns, and aging. This is useful to prevent and/or treat skin inflammation, aging, and other skin and hair damage mediated by free radicals.

The composition of fatty moieties in OFTG is as follows: Linoleic Acid comprises 38%–42%; Oleic Acid comprises 38%–42%; and Palmitic Acid comprises 14%–17% of the total fatty acid content. Free fatty acids are typically present at 8%. The fatty acid composition profile is of importance because it is close to that of the principal constituents of human skin surface lipids that play a key role in maintaining the normal barrier function of healthy skin.

Surfactants and fatty derivatives useful as emollients, dispersants, emulsifiers, and conditioners for hair and skin care products are commonly produced from a wide variety of fatty acids, fatty alcohols and amines, polyamines, dialkyl propylamines, alkanolamines, etc. Unless otherwise specified herein, the term "derivatives" is a broad term meant to include surfactants, nonsurface active esters, and ester emollients.

The following list of reactants and their respective derivatives such as esters, amides, betaines, quaternaries, etc., is exemplary of the type of reactants and derivatives on which the emollient surfactants and derivatives may be based, and, as such, is not to be considered limiting.

Group A (Reactants): Fatty acids or methyl esters of fatty acids or fatty oils sourced from naturally renewable fatty triglycerides of oats. A preferred source is oat seeds for oat-based triglycerides.

Group B (Reactants) may be selected from the group consisting of: Alkanolamines such as Monoethanolamine, Diethanolamine; Dialkylaminopropylamines such as Dimethyl Aminopropyl Amine; Polyamines such as Diethylene Triamine, Triethylene Tetramine; Primary and Secondary amines; and Fatty Alcohols (linear and/or branched) (C8–C22 alcohols).

The preferred reactants used in preparing the surfactants and derivatives of the invention are selected from the group consisting of:

A. OFTG and Monoethanolamine which are reacted to form a product whose proposed INCI name is oat-amide-MEA, tradename NATRLFINE® A, Finetex, Inc., Elmwood Park, N.J.

B. OFTG and Diethanolamine.
C. OFTG and Monoisopropanolamine.
D. OFTG and Diisopropanolamine.
E. OFTG and Dimethylaminopropylamine which are reacted to form a product whose proposed INCI name is oatamidopropyldimethylamine, whose tradename is NATRLFINE® MD, Finetex, Inc., Elmwood Park, N.J.
F. OFTG and IsoStearyl Alcohol.
G. OFTG Methylated and IsoStearyl Alcohol which are reacted to form a product whose proposed INCI name is IsoStearyl Oat Fatty Ester, tradename NATRLFINE® E-18, Finetex, Inc., Elmwood Park, N.J.
H. Reaction Product of (e) above (i.e., NATRLFINE® MD) and Sodium Monochloroacetate, which are reacted to form a product whose proposed INCI name is oatamidopropylbetaine, tradename NATRLFINE® AB-40, Finetex, Inc., Elmwood Park, N.J.
I. Reaction product of oatamidopropyl dimethyl amine and diethylsulfate, which are reacted to form a product whose proposed INCI name is Oat-amidopropylDiemthyl Ethyl Ethosulfate, tradename NATRLFINE® Q, Finetex, Inc., Elmwood Park, N.J.
J. Reaction product of Oat Amide-MEA-Maleate and Sodium Sulfite, which are reacted to form a product whose proposed INCI name is Disodium Oat-Amide-MEA-Sulfosuccinate, tradename NATRLFINE® SS, Finetex, Inc., Elmwood Park, N.J.

The most preferred reactants are A, E, G, H, I and J.

Reactants A and B are used in either exact stoichiometric proportions, or Reactant A (that is, OFTG) is used in some excess over Reactant B, so that there is no or negligible amounts of free Reactant B as residual in the finished product of the invention.

The novel oat lipid based surfactants and derivatives produced by the process of the invention include:

Group C: The Derivatives of Groups A & B Reactants include the following:

Monoethanolamides, Diethanolamides, Polyamides, Tertiary Acyl Amido Amines, e.g., Acyl Amidopropyl Dimethyl Amines, Amidopropyl Betaines, Amidopropyl Quaternaries, Esters with fatty alcohols (linear and/or branched) and Sulfosuccinamates.

OFTG is used in different ways to produce many of the aforementioned surface active derivatives, or non-surface active esters, and ester emollients. Among the surface active derivatives are:

Monoethanolamides, Monoisopropanolamides
Diethanolamides, Diisopropanolamides
Acyl (Oat Fatty based) Amidopropyl Dimethyl Amines
Betaines
Quaternary Ammonium Compounds
Sulfosuccinamates
Polyamides from Polyamines Among the non-surface active esters, and ester emollients produced by process of invention are:

Esters with Fatty Alcohols

For example, derivatives such as amides of OFTG/Monoethanolamine; Acyl Amidopropyl Dimethyl Amines of OFTG as Cationic Surfactants; Betaines based on OFTG; Esters of QFTG based Fatty Acids and Isostearyl Alcohol; Quaternaries based on OFTG based Amido-propyl Dimethyl Amine; Sulfosuccinamates based on OFTG—MEA Amides; and Sulfosuccinamates based on OFTG—Iso Propanolamines have been prepared. Derivatives may also include those involving other reactive groups known to those skilled in the art.

In a specific embodiment, and by way of illustration, this invention contemplates the production of the following surfactants and derivatives:

1. NATRLFINE® A (proposed INCI name: oat-amide-MEA) is the reaction product of OFTG and Monoethanolamine. It is also called OatFattyAmide of Monoethanolamine. It has the following structure:

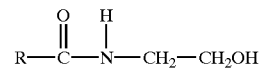

where R=oat fatty acids group.

2. NATRLFINE® T-1 (proposed INCI name: QAT-AMIDE-MEA and Sodium Cocoyl Methyl Taurate) is a blend or mixture of NATRLFINE® A and Sodium Cocoyl Methyl Taurate.

The structure of Sodium Cocoyl Methyl Taurate is:

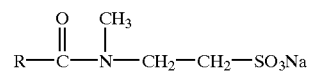

where R=Cocoyl group.

3. NATRLFINE® MD (whose proposed INCI name is oatamidopropyldimethylamine) is the reaction product of OFTG and Dimethylaminopropylamine. It has the following structure:

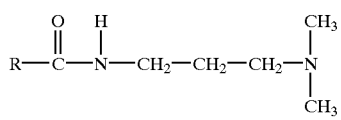

where R=Oat Fatty Acids group.

4. NATRLFINE® E-18 (proposed INCI name: IsoStearyl Oat Fatty Ester) is the reaction product of OFTG Methylated and IsoStearyl Alcohol. It has the following structure:

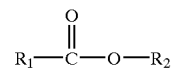

where
$R_1$=Oat Fatty Acids group; and
$R_2$=IsoStearyl Group.

5. NATRLFINE® AB-40 (proposed INCI name: oatamidopropylbetaine) is a betaine of oatamidopropyldimethylamine ester having the following structure:

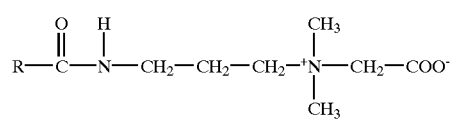

where R=Oat Fatty Acids group.

6. NATRLFINE® SS (proposed INCI name: Disodium Oat-Amide-MEA-Sulfosuccinate) is the reaction product of Oat Amide-MEA-Maleate and Sodium Sulfite. It has the following structure:

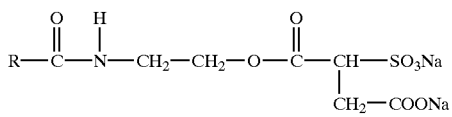

where R=Oat Fatty Acids group.

7. NATRLFINE® Q (proposed INCI name: Oat-AmidopropylDimethyl Ethyl Ethosulfate) is a reaction product of oatamidopropyl dimethyl amine and diethylsulfate having the following structure:

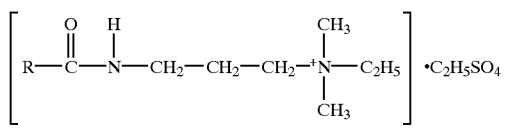

where R=Oat Fatty Acids group.

The derivatives have shown usefulness similar to conventional amides and betaines with the additional benefits of being mild to the skin. Also, skin feel is even better than using conventional derivatives.

Some of these surfactants and derivatives are used in skin care and hair care formulations and dermatological preparations. Personal care formulations prepared according to the invention, which contain the surfactants and derivatives added thereto, can be formed, without limitation, into applications such as solutions, emulsions, gels, solids, emulsions, aerosols, powders, creams, granules, or tablets.

Mildness and emolliency of these derivatives is of importance to the improved skin and hair care products including the surfactants and derivatives of the invention. The inherent presence of natural antioxidants and vitamin factors is the distinct difference in the use of OFTG as opposed to other commonly used fatty triglycerides. One other major aspect of derivatives of this invention is their very, very low to negligible toxicological effects indicating their mildness to skin care products.

Thus, the advantages of the derivatives of the invention include:

Made from naturally renewable source
Mildness of the derivatives
Possible antioxidancy activity
Mildness of the formulations containing the derivatives
Very low toxicological profile
Low irritation Thus, the novel oat-based surfactants and derivatives of this invention have unique properties in that they are mild to the skin, have very low to negligible toxicological effects, and natural antioxidants and vitamin factors are inherently present. These properties make these derivatives useful as a vehicle or carrier, dispersants, emulsifiers, emollient, solubilizer and conditioners for skin care and hair care formulations such as hair creams, hand cleaners, bath oils, suntan oils, anti-perspirants, perfumes, colognes, cold creams, electric pre-shaves, eye and throat oils, finger nail polish, topical pharmaceutical ointments, lipsticks, stick rouge, skin lotions and creams, skin moisturizers, cleansing creams, and after-bath splash and lotions, as well as other formulations. The foregoing list is only exemplary of the type of compositions in which the oat-based surfactants and derivatives of this invention may be used, and, as such, is not to be considered limiting.

The amount of such oat-based surfactants and derivatives to be used in such compositions is dependent on the type of hair care and skin care compositions, the desired dosage or amount of active ingredient to be delivered, the type and quantity of other ingredients, such as cosmetic ingredients used, the amount and type of functional additives that are utilized, the user's skin and hair type, and the severity and extent of the skin or hair condition, and other parameters that will be apparent to those skilled in the art. Generally, compositions containing the oat-based surfactants and derivatives of the invention are topically applied in effective amounts to the affected areas of the skin or to hair. Typically, the amount of surfactants and derivatives used ranges from about 1.0% to about 30.0%, by weight, of the skin care compositions. For example, a facial cream may only have about 5.0%, while a massage oil may have up to about 20% by weight. Still higher amounts may be used in, for example, bath oils, e.g. 50%.

Further, the oat-based surfactants and derivatives of this invention possess other unusual physio-chemical properties, which can make them suitable for use as emollient carriers in cosmetic formulations, and for use as solvents and emollient carriers in general cleaning compositions, such as in hand, face, and body creams and lotions. Thus, the oat-based surfactants and derivatives described herein may serve not only as emollients and carriers, but may also exhibit one or more other functions.

The surfactants and derivatives of the invention have properties such as, being less greasy, less oily, low toxicity, ease of emulsification, acid and alkaline stability, the ability to form gels with suspending agents, water solubility/dispersibility, and the ability to act as solvents for many common skin and hair care ingredients.

The following are non-limiting examples of processes for preparing the surfactant and derivative compositions of the invention (Examples 1 to 11), toxicology results for several of said compositions (Example 12), as well as uses of the compositions in specific cosmetic or personal care product formulations (Examples 13 to 19). In the Examples, as well as throughout this application, the chemical and scientific symbols have their customary meanings and all percents are weight percents unless otherwise specified.

Example Nos. 1 through 11 identify surfactants and derivatives produced by the process of the invention. For ease of identification, each ester is identified by both an Example Number and a Reference No., where applicable. This identification system is used in the subsequent Tables Nos. I through VII, as set forth in Examples 13 through 19.

Although the Examples use only selected compounds and formulations, it should be understood that the examples are illustrative and not limited. Thus, any of the aforementioned Reactants A and B may be substituted according to the teachings of this invention in the following Examples.

EXAMPLE #1

(117-16)
Preparation of Monoethanolamide of Oat Fatty Triglyceride (OFTG) (Trade Name: Natrlfine® A) (Proposed INCI Name: Oat-Amide-MEA)

405.30 gms. of Oat Fatty Triglyceride (OFTG, also called Oat Fatty Oil, available under the trade name of Microat® afa Complex from Nurture, Inc. of Missoula, Mont.) were charged to a one liter round bottom 4-neck flask with distillation assembly. To this was added 84.65 gms. Monoethanolamine (MEA) and 10.05 gms. Sodium Methylate 25% w/w in Methanol. Reaction mass was heated under nitrogen to between 105° C. and 120° C. Reaction was kept at between 105° C. and 120° C. over a period of 5 hours until the alkalinity was about 35 mg KOH/g.

This was a dark brown material that solidified upon cooling. The total mass collected was 453 gms. The distillate of free methanol was approximately 7.5 gms.

EXAMPLE #2
(117-36)
Preparation of Monoethanolamide of OFTG (Trade NATRLFINE® A)

486.36 gms. of Oat Fatty Triglyceride (OFTG, also called Oat Fatty Oil, available under the trade name of Microat® afa Complex from Nurture, Inc. of Missoula, Mont.) was charged to a one liter round bottom 4-neck flask with distillation assembly. This was brought to a temperature of 45° C. under nitrogen. To this was added 101.64 gms. Monoethanolamine (MEA) and 12.00 gms. of Sodium Methylate 25% w/w in Methanol. Reaction mass was first carried out at 110° C. for approximately 3 hours and then further reacted at 110° C.–120° C. for 3 hours. A mild vacuum of 5"–10" Hg. was applied to remove the methanol. The reaction mass showed alkalinity of 31.63 mg KOH/g.

The mass yield was 587 gms. as an amide (i.e., monoethanolamide ide of OFTG) with approximately 10 gms. methanol from the catalyst solution used, i.e., distillate of free methanol was 10 gms.

EXAMPLE #3
(117-21)
Preparation of Methyl Ester of Oat Fatty Triglyceride (OFTG)

440.35 gms. of Oat Fatty Triglyceride (OFTG, also called Oat Fatty Oil, available under the trade name of Microat® afa Complex from Nurture, Inc. of Missoula, Mont.) were charged to a one liter round bottom 4-neck flask with distillation assembly under nitrogen. Heated to 82° C. To this was added 54.65 gms. of Methanol and 5 gms. of Potassium Hydroxide Flakes. Reaction mass was then mixed at 78° C.–82° C. for ½ hour. Allowed to stand for 3–4 hours and the bottom glycerine layer was removed. The top layer, upon further standing, was a clear liquid methyl ester of the oat fatty oil. The residue from the methyl ester layer was approximately 143 gms. The yield as methyl ester was 380.5 gms. of the top clear liquid. This was further subjected to distillation for removal of methanol, which collection was approximately 20 gms.

The finished filtered yield of the methyl ester was 359 gms. with refractive index of 1.4590.

EXAMPLE #4
(117-23)
Isostearyl Ester of OFTG Fatty Acids (Proposed INCI Name: IsoStearylOatFatty Ester) Trade Name: NATRLFINE® E-18)

254.40 gms. of Methyl Ester of Example #3 was charged to one liter reaction flask with distillation assembly. To this was added under nitrogen 235.60 gms. of Isostearyl Alcohol and 10.0 gms. of Sodium Methylate 25% in Methanol. The mass was reacted at 130° C. for approximately 2 hours and any free methanol or methanol of reaction was removed by distillation at reduced pressure of 10" Hg. The methanol distillate collected was approximately 7.5 gms. with some leftover condensate in the condenser. The mass was further refurbished with 6.0 gms. of Sodium Methylate and further reacted at 150° C.–160° C. with vacuum of 10"–15" Hg. The ester was then collected which showed solidification characteristics. The 395 gm. of isostearyl ester was then washed with 100 gms. water containing 10 gms. Sodium Chloride and 12.5 gms. of concentrated Hydrochloric Acid adjusted to pH 6.00. Separation occurred at 70° C.–75° C. Allowed to stand. Separated bottom layer weighing 100 gms. (dark water layer). A second wash was given with 200 gms. water and 30 gms. sodium chloride. Bottom aqueous layer of 280 gms. was drained and the top layer of the ester collected was 372 gms.

This wet ester was then dried in the reaction flask at 115° C.–125° C. at reduced pressure of 15"–25" Hg. The ester was then cooled and filtered using diatomaceous earth. A liquid of an amber color was obtained. The net filtered yield was 343.3 gms.

EXAMPLE #5
(117-25)
Preparation of Fluid Delivery System for Oat-Amide-MEA of Example #1 (Trade Name NATRLFINE® T-1) (INCI Name: Oat-Amide-MEA and Sodium Cocoyl Methyl Taurate)

The solid amide of Example #1 is Oat-Amide-MEA. In this Example, the amide is blended with aqueous solution of Sodium-N-Methyl-N-Cocoyl Taurate resulting in a fluid, flowable dispersion paste. Thus, 8 gms. of Oat-Amide-MEA of Example #1 was mixed at 70° C. with a mixture of 70 gms. of Sodium-N-Methyl-N-Cocoyl Taurate (TAURANOL® WS CONC. from Finetex, Inc. of Elmwood Park, N.J.) and 22 gms. of water. A smooth off-white paste with very good flow was obtained upon cooling with mixing.

EXAMPLE #6
(117-54)
Preparation of a Blend of Oat-Amide-MEA and Sodium Methyl Cocoyl Taurate (Trade Name: NATRLFINE® T-1) (Proposed INCI Name: Oat-Amide-MEA and Sodium Cocoyl Methyl Taurate)

Blend of Oat-Amide-MEA and cocoyl taurate, 700 gms. of TAURANOL® WS CONC. (Sodium-N-Methyl-Cocoyl Taurate), 220 gms. of water and 80 gms. Oat-Amide-MEA of Example #1 were mixed at 80° C.–85° C. All of the solid particulate matter dissolved, giving an amber gel at 40° C. Upon cooling, a smooth off-white paste was obtained. Collected yield was 995 gms. of this mixture.

EXAMPLE #7
(117-38)
Amido Amine of OFTG and Dimethyl Amino Propyl Amine Trade Name: NATRLFINE® MD (Proposed INCI Name: Oat-Amidopropyldimethylmine)

426 gms. of Oat Fatty Triglyceride (OFTG) was charged to 1 liter reaction flask with distillation assembly. To this, under nitrogen, was added, at 70° C., 162 gms. of Dimethyl Amino Propyl Amine (DMAPA) and 12 gms. Sodium Methylate 25% in Methanol. This mass was heated further to 150° C. and reacted over a period of about 5 hours. The final alkalinity was 142 mg KOH/g which resulted after applying a vacuum to remove the free DMAPA. The distillate collected was 25.50 gms. which was mostly DMAPA. The yield of this amido amine product of this reaction was 551 gms. and a residue of approximately 37 gms of byproduct. Thus the total was 588 gms. as collected yield.

EXAMPLE #8
(117-40)
Processing of Residue of Example #7

The high titer residue of Example #7 was diluted with water in the ratio of 37 gms. residue and 870 gms. water, totaling 907 gms. of the mixture.

A. The above mixture was a thin dispersion that showed a tremendous lubricity on skin when cleaning the hands under tap water. The dispersion has a slight viscous body to the mass. The dispersion also has a gelatinous flow indicating similarity to that shown by B-Glucan containing starches/proteins originating from oats, as is known in the art.

B. The dispersion was mixed in a 1:1 ratio with cocobetaine (McIntyre Group, University Park, Ill.) and was a clear solution with small gelatinous particles which easily disperse. This mixture gave excellent foaming for washing under tap water and left a smooth, silky feel on hands, especially on dry hands.

C. The dispersion was also cleared with minor additions of citric acid. Such clear solution also gave excellent foaming under tap water and hands washed with this clear liquid had distinct softer feel when wet and also when dry.

D. The dispersion, upon standing, shows sedimentation which re-disperses upon mixing. Also, the addition of citric acid permits the dispersion to become a clear liquid.

The exhibited properties indicate the derivative of the reaction of Example #7 is the major component of this dispersion.

EXAMPLE #9
(117-42)
Preparation of Betaine of OFTG-DMAPA (Trade Name: NATRLFINE® AB-40) (Proposed INCI Name: Oatamidopropyl Betaine)

To a two liter reaction flask, with mixer and condenser, was added 325.2 gms. water and 43.15 gms. of sodium monochloroacetate at 25° C. Mixture was kept under stirring until all of the sodium monochloroacetate was dissolved. The solution was then heated and brought to 60° C. To this was then added 131.64 gms. of the amido amine product of Example #7. The temperature was brought to and maintained at 83° C.–85° C. The mixture was a thick paste. An additional 200 gms. water and 103 gms. 1,3-Butylene Glycol was added to fluidize the same. The reaction was maintained at 80° C.–85° C. for about 4–5 hours. The reaction showed 2.86% sodium chloride and 60% moisture as water by Karl Fisher titration. The yield was 733 gms. of the liquid betaine.

EXAMPLE #10
(117-55)
Preparation of Oat Amidopropyl Dimethyl Amine Trade Name: NATRLFINE® MD (Proposed INCI Name: Oatamidopropyldimethylamine) (Also Called Acyl Amidopropyl Dimethyl Amine)

Reaction flask of 2000 ml. capacity, with distillation assembly and mixer was set up under nitrogen. To this was added 852 gms. of Microat® afa Complex (Nurture, Inc., Missoula, Mont.) which is oat fatty oil, also called Oat Fatty Triglyceride (OFTG). Heated to 70° C. under nitrogen. To this was added 324 ms. Dimethyl Amino Propyl Amine (DMAPA) and 24 gms. Sodium ethylate 25% in Methanol. Temperature was brought to 120° C.–125° C. over 45 minutes. Heat input was adjusted to reach 150° C. over the next 30–45 minutes. Reaction was continued at 145° C.–150° C. 4 hours with use of vacuum. The reduced pressure ranging from 5" to 22" Hg. was used progressively to remove the free DMAPA. The yield, upon cooling, was 1097.6 gms. The distillate collected was 52 gms. which was almost pure DMAPA. The final product had an alkalinity of 160.43 mg KOH/g.

EXAMPLE #11
(117-59)
Preparation of Betaine-Derivative from Intermediate of Example #10 (Trade Name: Natrlfine® AB-40) (Proposed INCI Name: Oatamidopropylbetaine)

To a two liter reaction flask was added 654.0 gms. water and 53.7 gms. Sodium Monochloroacetate (SMCA). All SMCA was dissolved at 25° C. To this was added 128.3 gms. 1,3-Butylene Glycol. A clear liquid was formed. The pre-melted 164.0 gms. of the product of Example #10 were added to the mixture at 70° C.–72° C.; the addition was done in three portions. First portion was 82 gms.; the second portion was 50 gms.; and the third portion was 32 gms. These additions were done at 85°–86° C. and over a period of approximately one hour. The reaction mass was then held at 85° C. for further 2 hours. The alkalinity was found to be 13.94 mg KOH/g and acidity, i.e., acid value was almost none. An amber liquid with 2.66% Sodium Chloride and 66.65% of water by Karl Fisher titration was obtained. The net yield was 995 gms. as a Betaine.

Table I compares various properties and yields of the preparations of Examples 1 through 11.

TABLE I

TABLE OF PROPERTIES AND YIELDS OF PREPARATIONS OF EXAMPLES 1–11

| EXAMPLE NO. | REFRACTIVE INDEX | APPEARANCE | COLOR | ALKALINITY mgmKOH/gm | % YIELD ON TOTAL CHARGE |
|---|---|---|---|---|---|
| 1 | — | solid | dark amber | 35.00 | 90.6 |
| 2 | — | solid | dark amber | 31.63 | 97.83 |
| 3 | 1.4590 | liquid | light yellow | — | 71.80 |
| 4 | — | liquid | amber | — | 67.85 |
| 5 | | paste | off-white | — | 100 |
| 6 | | paste | off-white | — | 100 |
| 7 | | paste | amber | 142 | 98 |
| 8 | — | — | — | — | — |
| 9 | | liquid | lt. yellow | — | 100 (60% moisture) |
| 10 | | paste | amber | 160.43 | 91.47 |
| 11 | | liquid | amber | 13.94 | 99.50 (66.65% moisture) |

EXAMPLE # 11A (117-155)

Preparation of Oat Amidopropyl Dimethyl Ethyl Ethosulfate Quaternary (Proposed INCI Name) (Trade Name: Natrlfine® Q)

In a 4-neck 1 liter flask equipped with stirrer, condenser, nitrogen inlet and thermometer was added under nitrogen 175 gms. of oatamidopropyl dimethyl amine (product of Ex. 7 and 11) and 200 gms. of water and 50 gms. of butylene glycol. This was mixed and the mixture was brought to 60° C. To this mixture at 60° C. was added 73 gms. of Diethylsulfate. Reaction mixture was kept at between 90° C.–105° C. Any exotherm was controlled by manipulating the heating mantle to maintain temperature below 100° C. Reaction continued for about 3 hrs. when alkalinity was 6.29 mgms. KOH/gm. The amber liquid so obtained was completely water soluble and foamed heavily upon dilution with water. The yield was 490 gms. with moisture at 40%.

EXAMPLE #11B (122-164)

Preparation of Oat-Amide-MIPA (i.e., Monoisopropanolamide of OFTG) (Proposed INCI Name)

A one liter round bottom 4-neck flask with distillation assembly was charged with 405.3 gms. of Oat-Fatty Triglyceride (OFTG, also called Microat afa complex from Nurture, Inc., Missoula, Mont.). To this was added 104.07 gms of Monoisopropanolamine and 10.05 gms. of Sodium Methylate 25% w/w solution in methanol. Reaction mass was heated under nitrogen to between 105° C. and 120° C. over a period of 5 hrs. until the alkalinity was about 35 mgms. KOH/gm. This was a dark brown material that solidified upon cooling. The total mass collected was 504 gms. The distillate of free methanol was approximately 7.5 gms.

EXAMPLE #11C (122-166)

Preparation of Oat-Amide-MEA-Maleate Intermediate

To a 4-neck round bottom flask of 500 ml. capacity equipped with stirrer, condenser, and nitrogen inlet was added 105.3 gms. of oat amide-MEA (i.e., product of Ex. 1 and 2). Heated mildly to 70° C. Added 30.45 gms. of Maleic Anhydride. Reaction exothermed to 80° C.–85° C. Mixture was held at 85° C. for 1 hr.; acidity was found to be 128 mgm. KOH/gm. This was discharged as a dark amber liquid and the net yield weighed at 135.75 gms.

EXAMPLE #11D (122-167)

Preparation of Disodium Oat-Amide-MEA-Sulfosuccinate (Proposed INCI Name) Trade Name: NATRLFINE® SS A one liter round bottom flask equipped with condenser, nitrogen inlet and stirrer was charged with 325.58 gms. of water and 39.15 gms. of sodium sulfite. The sulfite crystals were completely dissolved. To this was added 135.75 gms. of Oat Amide-MEA-Maleate Intermediate (product of Ex. # 11C). The reaction mixture was held at 70° C.–85° C. with the controlled addition of the oat amide-MEA-Maleate intermediate. The mixture was gelled initially which fluidized as the reaction continued with the conversion. The yield was 500 gms. net in the flask with pH of 6.5 and showed 35% solids. It was a thick dispersion. A further dilution with additional 75 gms. of water was done. A fluid light yellow dispersion was obtained. This product gave a very good rich foam when dissolved in water and further diluted for washing hands. The skin feel was also very smooth and pleasant without defatting effects.

EXAMPLE #12

The oat based surfactants/derivatives of the invention have undergone toxicology testing, as follows. These studies were done using non-animal test protocols. Skin Tissue Model and Ocular Tissue Model by Mat-Tek Corporation in-vitro systems were used for dermal and ocular irritation studies.

1. NATRLFINE® T-1 (Example Nos. 5 & 6)

This is a fluid delivery system for Oat-Amide-MEA of Example Nos. 1 & 2 blended with Sodium N-Methyl-N-Cocoyl Taurate. TAURANOL® WS CONC. was used as a comparative control.

2. NATRLFINE® AB-40 (Example #9)

A betaine based on the oat fatty dimethyl amido amine, also called "betaine of OFTG-DMAPA".

A commercially available coco-betaine (Schercotaine CAB from Scher Chemicals, Clifton, N.J.) was used for comparative purposes. This commercial betaine is identified as Expt. Product 118-24.

Dermal Tox Summary

| | | Irritation Ratings/Classifications |
|---|---|---|
| 1. | Positive Control[1] | Moderate to mild range |
| 2. | NATRLFINE ® T-1 | Moderate to mild range |
| 3. | TAURANOL ® WS CONC. | Moderate to mild range |
| 4. | NATRLFINE ® AB-40 | Very mild range |
| 5. | Commercial Coco-Betaine Expt. Product 118-24 | Moderate to mild range |

[1]The Positive Control is 1.0% Triton X-100, (nonylphenol 10 EO Ethoxylate, a known irritant.

The Positive Control is 1.0% Triton X-100, (nonylphenol 10 EO Ethoxylate, a known irritant.

Dermal Ratings

NATRLFINE® T-1 is a blended oat-amide with cocoyl taurate, yet it has not deteriorated the mildness characteristics of the cocoyl taurate. The ratings for the cocoyl taurate and for NATRLFINE® T-1 are the same, i.e., moderate to mild range.

NATRLFINE AB-40, a betaine based on oat fatty lipid, shows a rating of very mild range vs. the commercial coco-betaine (Schercotaine CAB from Scher Chemicals, Clifton, N.J.) which is in the moderate to mild range. This demonstrates the superiority of the compounds of the invention in terms of dermal toxicology.

Ocular Tox Summary

| | | Irritation Ratings/Classifications |
|---|---|---|
| 1. | Positive Control[1] | Moderate to mild range |
| 2. | NATRLFINE ® T-1 | Minimal Irritancy |
| 3. | TAURANOL ® WS CONC. | Minimal irritancy |

-continued

| | Ocular Tox Summary | |
|---|---|---|
| | | Irritation Ratings/Classifications |
| 4. | NATRLFINE ® AB-40 | Minimal irritancy |
| 5. | Commercial Coco-Betaine Expt. Product 118-24 | Mild irritancy |

[1]The Positive Control is 1.0% Triton X-100, (nonylphenol 10 EO Ethoxylate) which is a known irritant.

Ocular Ratings

NATRLFINE® T-1 again has not deteriorated the mildness characteristics of cocoyl taurate. Irritancy is minimal as in the cocoyl taurate.

Personal Care Product Formulation Containing Novel Oat Lipid Based Surfactants and Derivatives OAT LIPID BASED SURFACTANTS AND DERIVATIVES To further demonstrate the superiority of the surfactants and derivatives of the invention, a series of formulations was prepared comparing the skin feel, emolliency, slip and foaming characteristics of various personal care products formulated with the compositions of the invention, and with other commercially available surfactants and derivatives which are commonly used in such types of products. The products specifically included facial cleanser, conditioning shampoo, shower gel, skin cleansing gel, shower and bath gel, and 2 in 1 conditioning shampoo. These are considered to be representative of formulations wherein the surfactants and derivatives of the invention find application.

Example #13

(Ref. No. 103-020)

Gentle Facial Cleanser

This is a comparison of NATRLFINE® T-1 (Example #5) to Disodium Cocoamphodiacetate, a commercially available amphoteric betaine from McIntyre Group, University Park, Ill.

TABLE II

| Ingredients/Tradename or Generic Name | A | B |
|---|---|---|
| 1. Water (deionized) | 91.39 | 91.39 |
| 2. NATRLFINE ® T-1 | — | 8.00 |
| 3. Pluracare L-64 | 2.00 | — |
| 4. Mackam 2C | 6.00 | — |
| 5. Citric Acid | 0.01 | 0.01 |
| 6. Ajidew N-50 | 0.10 | 0.10 |
| 7. Germall Plus | 0.20 | 0.20 |
| 8. Ritapan DL | 0.10 | 0.10 |
| 9. Biopol HC | 0.20 | 0.20 |
| Total: | 100.00 | 100.00 |

Procedure

1. Charge water (1) and heat to 70° C. to 75° C.
2. Add other ingredients 2 through 6 in the order set forth.
3. Bring temperature to 70° C.–75° C.
4. Mix well for uniformity.
5. Cool to 45° C.
6. Add ingredients 7 through 10 in the order set forth above.
7. Mix gently, cooling to 35° C.

The properties of the two formulations A and B are as follows:

| | Formulation A | Formulation B |
|---|---|---|
| Appearance: | Clear Liquid | Liquid with Pearlescence |
| pH, as is: | 8.5 | 7.5 |
| Viscosity: | Very Thin Liquid | Very Thin Liquid |

Formulations A and B so prepared were tested for skin feel, emolliency, and slip on a scale of 1 to 5, with 1 representing the best and 5 representing poor results, as follows:

| | Formulation A | Formulation B |
|---|---|---|
| Skin Feel | 4 | 1 |
| Emolliency | 4 | 1 |
| Slip | 4 | 1 |

Formulation B, the product of the invention, gave superior skin feel, emolliency, and slip.

EXAMPLE #14

(Ref. No. 103-019)

Conditioning Shampoo

This is a comparison of NATRLFINE® AB-40 (Example #9) to Cocoamidopropylbetaine (CAPB), a commercially available betaine from McIntyre Group. Table III below sets forth the ingredients and test results follow.

TABLE III

| Ingredients/Tradename | A | B |
|---|---|---|
| Water (Deionized) | 55.700 | 53.700 |
| Citric Acid | 0.175 | 0.175 |
| Sodium Citrate | 0.500 | 0.500 |
| Versene Na2 crystals | 0.050 | 0.050 |
| Hydrosoy 2000SF | 0.100 | 0.100 |
| Standapol A | 36.000 | 36.000 |
| Mackam L Experimental Product 117-42 | 5.400 | — |
| NATRLFINE AB-40 (Example #9) | — | 5.400 |
| Mackamide LLM | 0.500 | 0.500 |
| Fragrance 808999 | 0.300 | 0.300 |
| Kathon CG | 0.025 | 0.025 |
| Sodium Chloride (20% Soln.) | 1.250 | 3.250 |
| Total: | 100.00 | 100.00 |

Procedure

1. Charge water (1) and heat to 70° C. to 75° C.
2. Add other ingredients 2 through 6 in the order listed above.
3. Bring temperature to 70° C.–75° C.
4. Mix well until uniform.
5. Cool to 45° C.
6. Add fragrance and preservative (Kathon CG).
7. Add sodium chloride.
8. Mix gently, cooling to 35° C.

The properties of the two formulations A and B are as follows:

|  | Formulation A | Formulation B |
|---|---|---|
| Appearance: | Clear Gel | Clear Gel |
| pH, as is: | 5.0 | 4.93 |
| Viscosity: | 1150 | 1460 |

Both Formulations A and B are clear, viscous gels, but Formulation B is more viscous.

Formulations A and B so prepared were tested for skin feel, emolliency, and slip on a scale of 1 to 5, with 1 representing the best and 5 representing poor results, as follows:

|  | Formulation A | Formulation B |
|---|---|---|
| Skin Feel (scalp) | 3 | 1 |
| Emolliency (scalp) | 3 | 1 |
| Slip (smoothness) | 3 | 1 |

Formulation B, the product of the invention, gave superior skin feel, emolliency, and slip.

EXAMPLE #15
(Ref. No. 103-021)
Shower Gel

This is a comparison of NATRLFINE AB-40 (Example #9) to Cocoamidopropylbetaine (CAPB), a commercially available betaine from McIntyre Group. Table IV below sets forth the ingredients and test results follow.

TABLE IV

| Ingredients/Tradename | A | B |
|---|---|---|
| Part A |  |  |
| Water (Deionized) | 20.800 | 20.800 |
| Versene 100 XL | 0.050 | 0.050 |
| Standapol ES-2 | 20.000 | 20.000 |
| Hamposyl L-30 | 20.000 | 20.000 |
| Crothix | 0.200 | 0.200 |
| Mackam L | 30.000 | — |
| NATRLFINE ® AB-40 (Example #9) | — | 30.000 |
| Glycerox HE | 3.000 | 3.000 |
| Germaben ® II | 1.000 | 1.000 |
| Part B |  |  |
| Citric Acid, 50% Solution | 0.450 | 0.450 |
| Mackamide LLM | 3.000 | 3.000 |
| Part C |  |  |
| Fragrance #154841-069D | 1.500 | 1.500 |
| (Green Tea) |  |  |
| Total: | 100.000 | 100.000 |

Procedure
1. Charge the ingredients of Part A starting with water.
2. Bring the temperature to 70° C. to 75° C.
3. Mix well until uniform.
4. Add ingredients of Part B and mix well, avoiding aeration.
5. Cool to 45° C. with gentle mixing.
6. Add ingredients of Part C.
7. Mix well (gently).
8. Allow to deaerate by standing at 45° C.
9. Cool to 35° C. to 35° C.

The properties of the two formulations A and B are as follows:

|  | Formulation A | Formulation B |
|---|---|---|
| Appearance: | Clear Gel | Clear Gel |
| pH, as is: | 5.61 | 5.85 |

Formulations A and B so prepared were tested for skin feel, emolliency, and slip on a scale of 1 to 5, with 1 representing the best and 5 representing poor results, as follows:

|  | Formulation A | Formulation B |
|---|---|---|
| Skin Feel | 4 | 1 |
| Emolliency | 4 | 1 |
| Slip | 4 | 1 |

Formulation B gave superior skin feel, emolliency, and slip.

EXAMPLE #16
(Ref. No. 117-134-A)
Clear and Mild Skin Cleansing Gel

This is a comparison of NATRLFINE® AB-40 (Oat Betaine Example #9) vs. CAPB when used in combination with NATRLFINE® T-1 (Example #5). Table V below sets forth the ingredients and test results follow.

TABLE V

| Ingredients/Tradename | 1 | 2 | 3 | 4 |
|---|---|---|---|---|
| Reference No. | 122-41 | 122-42 | 122-43 | 122-44 |
| Water (Deionized) | 50.5 | 50.5 | 50.5 | 50.5 |
| Standapol EA-2 | 15 | 15 | 15 | 15 |
| TAURANOL ® 1-78C | 6 | 6 | 6 | 6 |
| Cocobetaine | 10 | — | 10 | — |
| NATRLFINE AB-40 | — | 10 | — | 10 |
| NATRLFINE T-1 | 15 | 15 | — | 15 |
| TAURANOL ® WS CONC. | — | — | 15 | 15 |
| PEG-150 Pentaerythrityl Stearate | 2 | 2 | 2 | 2 |
| Germaben ® II | 0.5 | 0.5 | 0.5 | 0.5 |
| Baby Fragrance (1:5 in Propylene Glycol) | 1.0 | 1.0 | 1.0 | 1.0 |
| Total: | 100.0 | 100.0 | 100.0 | 100.0 |

Procedure
1. Charge water.
2. Heat to 70° C. to 75° C.
3. Add other ingredients in the order listed above.
4. Bring the temperature to 70° C. to 75° C.
5. Mix until clear.
6. Cool to 45° C.
7. Add Germaben II. Mix.
8. Cool to 35° C.

The properties of the four formulations 1–4 are as follows:

|  | 1 | 2 | 3 | 4 |
|---|---|---|---|---|
| Appearance: | Clear Gel | Clear Gel | Clear Gel | Clear Gel |
| pH, as is: | 6.10 | 6.24 | 5.74 | 6.16 |

-continued

|  | 1 | 2 | 3 | 4 |
|---|---|---|---|---|
| Viscosity cps: | 25000 | 34800 | 36400 | 31000 |

Formulations 1–4 so prepared were tested for skin feel, emolliency, and slip on a scale of 1 to 5, with 1 representing the best and 5 representing poor results, as follows:

|  | 1 | 2 | 3 | 4 |
|---|---|---|---|---|
| Skin Feel | 3 | 1 | 3 | 1 |
| Emolliency | 3 | 1 | 3 | 1 |
| Slip | 4 | 2 | 4 | 2 |

Formulation 2 gave superior skin feel, emolliency, and slip.

EXAMPLE #17

(Ref. No. 117-134-B)

Shower and Bath Gel

This is a comparison of oat based betaine and oat based ester emollient to commercial cocobetaine and commercial ester emollient. Table VI below sets forth the ingredients and test results follow.

TABLE VI

| Ingredients/Tradename | 1 | 2 | 3 | 4 |
|---|---|---|---|---|
| Reference No. | 122-45 | 122-46 | 122-45-A | 122-46-A |
| Part A |  |  |  |  |
| Water (Deionized) | 30.5 | 30.5 | 28.5 | 28.5 |
| Standapol ES-40 | 30 | 30 | 30 | 30 |
| TAURANOL ® 1-78C | 5 | 5 | 5 | 5 |
| Cocobetaine | 10 | — | 10 | — |
| NATRLFINE ® AB-40 | — | 10 | — | 10 |
| NATRLFINE ® T-1 | 20 | 20 | 20 | 20 |
| Part B |  |  |  |  |
| FINSOLV ® TN | 3 | — | 3 | — |
| NATRLFINE ® E-18 | — | 3 | — | 3 |
| CROTHIX Stearate | — | — | 2 | 2 |
| Part C |  |  |  |  |
| Germaben ® II | 0.5 | 0.5 | 0.5 | 0.5 |
| Baby Fragrance | 1.0 | 1.0 | 1.0 | 1.0 |
| (1:5 in Propylene Glycol) |  |  |  |  |
| Total: | 100.0 | 100.0 | 100.0 | 100.0 |

Procedure

1. Charge water.
2. Add ingredients of Part A.
3. Bring temperature to 70° C. to 750° C.
4. Add ester of Part B. Mix.
5. When all dissolved and clear, cool to 45° C.
6. Add ingredients of Part C. Mix.
7. Cool to 35° C.
8. Package.

The properties of the four formulations 1–4 are as follows:

|  | 1 | 2 | 3 | 4 |
|---|---|---|---|---|
| Appearance: | Thin Liquid | Thin Liquid | Viscous Liquid | Viscous Liquid |
| pH, as is: | 6.85 | 6.88 | 6.80 | 6.85 |
| Viscosity cps: | — | — | 9500 | 8900 |

EXAMPLE #18

(Ref. No. 117-134-C)

2 in 1 Clear Conditioning Shampoo

This is a comparison of NATRLFINE T-1 (Example #5) in conjunction with commercially available substantive quaternary ammonium compound. Table VII below sets forth the ingredients and test results follow.

TABLE VII

| Ingredients/Tradename | 1 | 2 | 3 | 4 |
|---|---|---|---|---|
| Reference No. | 122-47 | 122-48 | 122-49 | 0122-50 |
| Water (Deionized) | 42.80 | 42.80 | 42.80 | 42.80 |
| Standapol ES-40 | 30.00 | 30.00 | 30.00 | 30.00 |
| NATRLFINE T-1 | 20 | 20 | — | — |
| TAURANOL ® WS CONC. | — | — | 20 | 20 |
| FINQUAT ® CT4 | 5 | — | 5 | — |
| FINQUAT ® CT-P | — | 5 | — | 5 |
| PEG-150 Pentaerythrityl Stearate | 1.00 | 1.00 | 1.00 | 1.00 |
| DMDM Hydantoin | 0.20 | 0.20 | 0.20 | 0.20 |
| Baby Fragrance | 1.00 | 1.00 | 1.00 | 1.00 |
| (1:5 in Propylene Glycol) |  |  |  |  |
| Citric Acid, 25% for pH 6.0 | q.s. | q.s. | q.s. | q.s. |
| Total: | 100.0 | 100.0 | 100.0 | 100.0 |

Procedure

1. Charge water.
2. Heat to 70° C. to 75° C.
3. Add all ingredients except DMDM Hydantoin.
4. Mix well until dissolved.
5. Cool to 45° C.
6. Add DMDM Hydantoin.
7. Cool to below 35° C.
8. Adjust pH to 6.0.
9. Package.

The properties of the four formulations 1–4 are as follows:

|  | 1 | 2 | 3 | 4 |
|---|---|---|---|---|
| Appearance: | Clear Gel | Clear Gel | Clear Gel | Clear Gel |
| pH: | 6.25 | 6.25 | 6.25 | 6.25 |
| Viscosity cps: | 6500 | 2800 | 55 | 70 |

Viscosity after addition of 0.4% NaCl: 610 760

Formulations 1 and 2 gave superior skin feel, emolliency, and slip.

EXAMPLE #19

(Ref. No. 117-134-D)

Foam Tests on Oat Based Surfactants vs. Commercially Available Cocobetaines and Cocotaurates.

This is a comparison of foaming characteristics of oat based surfactants (NATRLFINE T-1 and NATRLFINE AB-40) vs. commercially available cocotaurates and cocobetaines (TAURANOL® WS CONC. from Finetex, Inc. and Cocobetaine from McIntyre Group).

The test comprises 0.1 gm. Surfactant in 100 ml. water. 500 ml. graduated cylinder with stopper. 10 strokes on the cylinder by hand. The results were measured in terms of foam height initially and after 5 minutes, the nature of the foam, and the durability of the foam.

The following products were compared:

NATRLFINE T-1=Sodium Methyl Cocoyl Taurate/Oat Amide MEA blended product
TAURALNOL WS. CONC.=Sodium Methyl Cocoyl Taurate
NATRLFINE AB-40=Oat Fatty Amidopropyl
COCOBETAINE=Cocoamidopropylbetaine

TABLE VIII

|  | NATRLFINE ® T-1 | TAURANOL ® WS CONC. | NATRLFINE ® AB-40 | COCOBETAINE |
|---|---|---|---|---|
| Initial | 200 mls. | 200 mls. | 150 mls. | 150 mls. |
| 5 Minutes | 100 mls. | 150 mls. | 120 mls. | 100 mls. |
| Durability of Foam | Stable; Residual | Stable; Residual | Stable; Uniform Thick Rich Foam; Residual 20 mls. | Scattered Top ½ thin Bottom ½ thick |
| ½ Hour | 75 mls. | 10–20 mls. Residual 70 mls. | | |
| Nature of Foam | Thick, Rich Dense Bubbles | Large Bubbles Scattered/Thin | Thick, Rich Dense Foam | Mixture of Thick and Thin Foam |

Note:
By "residual" is meant foam left after ½ hour waiting time.

NATRLFINE® T-1 and NATRLFINE® AB-40 are superior in foaming characteristics.

TABLE IX

IDENTIFICATION OF TRADE OR GENERIC LISTED PREPARATION INGREDIENTS

| TRADE OR GENERIC MATERIAL | IDENTIFICATION | SOURCE |
|---|---|---|
| Natrlfine ® T-1 | Oat-Amide-MEA and Sodium Cocoyl Methyl Taurate | Finetex, Inc. Elmwood Park, NJ |
| Pluracare L-64 | Poloxamer 184 | BASF, Mt. Olive, NJ |
| Mackam 2C | Disodium cocoamphodiacetate | McIntyre Group University Park, ILL |
| Ajidew N-50 | Sodium PCA (Pyrrolidone Carboxylic Acid) | Ajinomoto Paramus, NJ |
| Germal Plus | Diazolidinyl Urea & Iodopropynyl Butylcarbamate | ISP, Wayne, NJ |
| Ritapan DL | Panthenol | R.I.T.A. Chemical Woodstock, ILL |
| Biopol HC | Hyaluronic Acid & Collagen Complex | Brooks Industries S. Plainfield, NJ |
| Versene Na2 crystals | Disodium EDT | Dow Chemical Co. Midland, MI |
| Hydrosoy 2000SF | Hydrolyzed soy protein | Croda Parsippany, NJ |
| Standapol A | Ammonium lauryl sulfate | Cognis, Ambler, PA |
| Mackam L | Cocoamidopropyl betaine (CABP) | McIntyre Group University Park, ILL |
| Natrlfine AB-40 | Oatamidopropyl betaine | Finetex, Inc. Elmwood Park, NJ |
| Mackamide LLM | Lauramide DEA | McIntyre Group University Park, ILL |
| Fragrance 808999 | — | Manheimmer Teterboro, NJ |
| Kathon CG | Methylchloroisothiazolinone | Rohm & Haas Co. Philadelphia, PA |
| Versene 100 XL | Tetrasodium EDTA | Dow Chemical Co. Midland, MI |
| Standapol ES-2 | Sodium Laureth Sulfate | Cognis, Ambler, PA |
| Hamposyl L-30 | Sodium Lauroyl Sarcosinate | Hampshire Chem. Co. Lexington, MA |
| Crothix | PEG-150 Pentaerythrityl Tetrastearate | Croda, Parsippany, NJ |
| Glycerox HE | PEG-7-Glyceryl Cocoate | Croda, Parsippany, NJ |
| Germaben II | Propylene Glycol and Diazolidinyl Urea and Methylparaben and Propylparaben | ISP, Wayne, NJ |
| Fragrance #154841-069D | Fragrance and Orange oil and Lavandin Oil and Basil Oil | Manheimmer Teterboro, NJ |

TABLE IX-continued

IDENTIFICATION OF TRADE OR GENERIC LISTED PREPARATION INGREDIENTS

| TRADE OR GENERIC MATERIAL | IDENTIFICATION | SOURCE |
|---|---|---|
| (Green Tea) | and Cedarwood Oil and Chamomile Oil | |
| Standapol EA-2 | Ammonium Laureth Sulfate | Cognis, Ambler, PA |
| Tauranol 1-78C | Sodium Cocoyl Isethionate | Finetex, Inc. Elmwood Park, NJ |
| Cocobetaine | Cocoamidopropyl betaine | McIntyre Group University Park, ILL |
| Tauranol WS CONC. | Sodium Cocoyl Methyl | Taurate Finetex, Inc. Elmwood Park, NJ |
| Finquat CT | Quaternium 75 | Finetex, Inc. Elmwood Park, NJ |
| Finquat CT-P | Quaternium 89 | Finetex, Inc. Elmwood Park, NJ |
| Finsolv TN | C12–15 Alkyl Benzoate | Finetex, Inc. Elmwood Park, NJ |
| Natrlfine E-18 | Isostearyl Oat-Fatty Ester | Finetex, Inc. Elmwood Park, NJ |
| — | PEG-150 Pentaerythrityl Stearate | Croda, Parsippany, NJ |
| Standapol ES-40 | Sodium Laureth Sulfate | Cognis, Ambler PA |
| DMDM Hydantoin | DMDM Hydantoin | Lonza, Fairlawn, NJ |

In conclusion, the surfactants and derivatives of the invention are surprisingly found to have excellent foaming characteristics.

It will be understood that the embodiments described herein are merely exemplary and that a person skilled in the art may make many variations and modifications without departing from the spirit and scope of the invention. For example, the invention is not intended to be strictly limited to the named reactants and catalysts, recited pH ranges, reaction temperatures, reaction conversion, or other parameters. Rather, the invention as claimed extends to many possible variations not specifically detailed. All such variations and modifications are intended to be included in the scope of the invention as described herein.

We claim:

1. An oat-lipid based product which is a mixture, said mixture formed by reacting oat fatty triglycerides and monoethanolamide, said oat-lipid based product comprising oat-amide-MEA represented by the following structure:

where R=oat fatty acids group.

2. An external skin care preparation comprising an oat-lipid based product as defined in claim 1.

3. A cosmetic hair care formulation comprising an oat-lipid based product as defined in claim 1.

4. A skin or hair care method comprising applying to the skin or hair a preparation or formulation comprising an oat-lipid based product as defined in claim 1.

5. An oat-lipid based product formed by blending monoethanolamide of oat fatty triglyceride and Sodium-N-Methyl-N-Cocoyl Taurate.

6. An external skin care preparation comprising an oat-lipid based product as defined in claim 5.

7. A cosmetic hair care formulation comprising an oat-lipid based product as defined in claim 5.

8. A skin or hair care method comprising applying to the skin or hair a preparation or formulation comprising an oat-lipid based product as defined in claim 5.

* * * * *